United States Patent [19]

Earl

[11] Patent Number: 4,486,351
[45] Date of Patent: Dec. 4, 1984

[54] USE OF POLYMERIC ETHYLENE OXIDES IN THE PREPARATION OF GLYCIDYL AZIDE POLYMER

[75] Inventor: Robert A. Earl, Salt Lake City, Utah
[73] Assignee: Hercules Incorporated, Wilmington, Del.
[21] Appl. No.: 561,394
[22] Filed: Dec. 14, 1983
[51] Int. Cl.$^3$ .............................................. C07C 117/00
[52] U.S. Cl. ..................................... 260/349; 525/410; 525/403
[58] Field of Search ................. 260/349; 525/410, 403
[56] References Cited

U.S. PATENT DOCUMENTS

| | | | |
|---|---|---|---|
| 3,645,917 | 2/1972 | Vandenberg | 260/2 D |
| 4,268,450 | 5/1981 | Frankel et al. | 260/349 |
| 4,405,762 | 9/1983 | Earl et al. | 525/410 |

*Primary Examiner*—Joseph Paul Brust
*Attorney, Agent, or Firm*—Edmund C. Ross, Jr.

[57] ABSTRACT

An improved process of preparing hydroxy-terminated aiphatic polyethers having pendant alkyl azide groups is disclosed. The process entails reacting metal azide and hydroxy-terminated aliphatic polyether having pendant haloalkyl groups at elevated temperatures. The improvement comprises using a liquid reaction medium that is relatively non-polar and comprises a polyalkyleneoxide having (a) a molecular weight above about 200 and (b) miscibility with the hydroxy-terminated aliphatic polyether having pendant haloalkyl groups at temperatures greater than about 80° C.

5 Claims, No Drawings

USE OF POLYMERIC ETHYLENE OXIDES IN THE PREPARATION OF GLYCIDYL AZIDE POLYMER

This invention relates to a process for making hydroxyterminated aliphatic polyethers having pendant alkyl axide groups.

Aprotic, polar solvents have been used in reacting polyepichlorohydrin and metal azide to form azide polymer, often referred to as glycidyl azide polyether. See, for example, U.S. Pat. No. 4,268,450 to Frankel and U.S. Pat. No. 3,645,917 to Vandenberg. When dimethyl formamide or dimethylsulfoxide is used as the reaction medium in the aforesaid reaction, the results have not been entirely satisfactory. (By "reaction medium" is meant the material in the reaction mixture which facilitates contact between reactants but does not undergo chemical change during the reaction). In particular, the resulting glycidyl azide polyether products have a tendency to decompose during storage at elevated temperatures. Such a tendency can make them unsuitable for use as a binder ingredient in rocket motor propellants. While the extact cause for the less than desired purity in the glycidyl azide polyether products is not known for certain, it is known that dimethylformamide decomposes slowly to dimethylamide and formic acid during prolonged heating and that dimethylsulfoxide has the ability to promote side reactions, including oxidation reactions. Moreover, separation of these aprotic, polar solvents from azide polymers can be difficult.

It has now been discovered that certain polyalkyleneoxides can be used as the reaction medium in reacting polyepichlorohydrin and metal azide, and that the resulting glycidyl azide polyether products have improved purity. The resulting products have a decreased tendency toward gasing during storage at elevated temperatures and, accordingly, are better suited as binder ingredients for rocket motor propellant formulations than those made using dimethylsulfoxide or dimethylformamide.

This invention thus relates generally to an improved process of preparing hydroxy-terminated aliphatic polyethers having pendant alkyl azid groups, the process comprising reaction of metal azide and hydroxy-terminated aliphatic polyether having pendant haloalkyl groups in the presence of liquid reaction medium at elevated temperatures. This invention, more particularly, relates to the improvement in such process where the reaction medium is relatively non-polar and comprises a polyalkylenoxide having (a) a molecular weight (number average) above about 200 and (b) miscibility with the hydroxy-terminated aliphatic polyeter having pendant haloalkyl groups at temperatures greater than about 80° C.

The process of this invention is particularly adapted to preparing glycidyl azide polyethers of improved purity for use as rocket motor propellant binder ingredients. In this embodiment, the improved process comprises forming a liquid reaction mixture consisting essentially of (i) polyethyleneoxide having a molecular weight (number average) above about 200, (ii) metal azide such as sodium azide and (iii) polyepichlorohydrin having a molecular weight between about 500 and 10,000 wherein (i) and (iii) are miscible in each other at temperatures greater than about 80° C.; (b) forming the glycidyl azide polyether in a reacted mixture by heating the reaction mixture at a temperature between about 80° C. and 120° C. for a time sufficient for displacement of the chloro groups of the polyepichlorohydrin with azido groups; (c) removing the polyethyleneoxide from the reacted mixture by aqueous washings; and (d) isolating the glycidyl azide polyether from the marked product of step (c).

Glycidyl azide polyether suitable for use as a binder ingredient in rocket motor propellant formulations is prepared in preferred practice of this invention. The glycidyl azide polyether is a polymer of the structure:

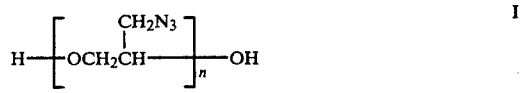

where the azido methyl group, —CH$_2$N$_3$, pends from the backbone and n is an integer ranging between about 10 and 100.

The glycidyl azide polyether is prepared by first forming a reaction mixture consisting essentially of (i) polyethyleneoxide having a molecular weight (number average) above about 200 (more preferably between about 300 and 1000), (ii) metal azide, preferably sodium azide; and (iii) polyepichlorohydrin having a molecular weight (number average) between about 500 and 10,000.

The polyethyleneoxide is a polymer of the structure:

wherein n is an integer ranging between about 5 and 25.

The polyepichlorohydrin has the structure:

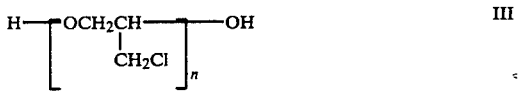

wherein the chloromethyl group, —CH$_2$Cl, pends from the backbone of the polymer and n is between about 10 and 100.

The metal azide is preferably sodium azide and of a particle size of about 100 mesh or less.

In forming the reaction mixture, the polyepichlorohydrin and polyethyleneoxide are selected so that they are miscible in each other; also oxygen gas is preferably removed from these ingredients by bubbling nitrogen through a mixture of them.

The weight ratio of the polyethyleneoxide to the polyepichlorohydrin in the reaction mixture is between 10:1 and 0.5:1. The metal azide is used in molar excess over the moles of chlorine present in the reaction mixture that are to be displaced. This molar ratio is preferably between about 1.05:1 to 1.5:1 azide to chloro for complete conversion of the chloromethyl groups to azidomethyl groups.

The reaction mixture is maintained at a temperature between about 80° to 120° C. with mixing and under an inert gas in forming the glycidyl azide polyether. The time of reaction to yield the glycidyl azide polymer ranges to about forty hours or more if no catalyst is present.

After the reaction is complete, the glycidyl azide polyether is isolated by standard separation techniques, including filtering and washing. For example, in separating the glycidyl azide polyether from the other components of the reacted mixture, the reacted mixture can be cooled to about 20° C. and diluted with an appropriate solvent prior to the washing. A preferred appropriate solvent is 1,1,1-trichloroethane since the polyethyleneoxide may be extracted out of this solvent into water.

The following examples illustrate this invention but are not intended to be limitations thereof.

EXAMPLE 1

Polyepichlorohydrin[1] (20 grams, 0.218 moles, molecular weight 3900) and sodium azide (15.6 grams, 0.238 moles) were added to 40 milliliters of a deoxygenated polyethyleneoxide (either diethylene glycol, 400 molecular weight polyethyleneoxide or 1000 molecular weight polyethyleneoxide) and the mixture heated with stirring under a nitrogen blanket at 95° C. Small samples (2 milliliters) were withdrawn at intervals and dissolved in 1,1,1-trichloroethane (20 milliliters) and the mixtures washed with water (4 times, 20 milliliters each time) to remove suspended salts and the polyethyleneoxide. The 1,1,1-trichloroethane solvent was then removed in vacuo and the residues subjected to quantitative azide analyses (5) to determine completeness in the converting polyepichlorohydrin to the glycidyl azide polyether. Table I summarizes the experimental results:

TABLE 1

| Reaction Media | Reaction Time (hrs) | % Conversion |
|---|---|---|
| Diethylene glycol[2] | 23 | 3 |
| | 47 | 5 |
| Polyethyleneoxide[3] | 23 | 88 |
| (molecular wt. 400) | 30 | 93 |
| | 40 | 100 |
| Polyethyleneoxide[4] | 23 | 71 |
| (molecular wt. 1000) | 30 | 84 |
| | 47 | 85 |
| | 54 | 89 |

(1) Used as received from 3M Co.
(2) Used as received from Aldrich Chemical.
(3) Used as received from Matheson, Coleman and Bell.

As can be seen, the diethylene glycol has a molecular weight (MW) too low to be effective as the reaction medium. On the other hand, the 1000 MW polyethyleneoxide performs somewhat less desirable than the 400 MW polyethyleneoxide. The polyepichlorohydrin is less soluble in the 1000 MW polyethyleneoxide as compared to the 400 MW polyethyleneoxide.

EXAMPLE 2

Polyepichlorohydrin[1] (92 grams, 1 mole, Mw=8,700) was dissolved in polyethyleneoxide [2] (184 milliliters) and deoxygenated by bubbling nitrogen through the solution for one hour. The mixture was then heated to 93° C. with mechanical stirring and sodium azide[3]. (71.5 g., 1.1 moles) was added on one addition. The mixture was stirred and heated (93° C.) under a blanket of nitrogen for 72 hours and then cooled to room temperature. The reacted mixture was then diluted with 1,1,1-trichloroethane (270 ml) and washed in succession with water (2×200 ml), 1:1 methanol-water (100 ml. volume to volume) and saturated sodium chloride solution (100 ml). The reacted mixture was then filtered through a dry-packed bed (2.5 cm. ×10 cm.) of Celite (a diatomaceous earth filter aid, Johns-Manville) to remove traces of turbidity. The filtrate was diluted to 500 ml with 1,1,1-trichloroethane and then passed through a glass column (4.0 cm ×30 cm), dry-packed with silica gel (100 g, pH 7, 60–200 mesh, Davidson Chemical Co.) and topped with 3 angstrom molecular sieves (Davidson Chemical Co.) and which had been preeluted with 1,1,1-trichloroethane (300 ml). The column was then eluted with additional 1,1,1-trichloroethane (250 ml). The combined eluates were concentrated in vacuo with final concentration being carried out for one hour at 0.5 torr and 51° C. Yield: 63.4 g (63.4%) of a pale yellow viscous polymer. Calculated for $C_3H_5N_3O$: %N, 42.45. Found: 42.32. The FT-ir spectrum showed a strong absorption at 2105 cm$^1$ for azide and the complete absence of any absorption at 740 cm$^{-1}$ for carbon-chlorine stretch indicating that 100% displacement of chloride by azide had taken place.

(1) Used as received from 3M Co.
(2) Used as received from Matheson, Coleman and Bell.
(3) Used as received from Aldrich Chemical.

What is claimed is:

1. A process of preparing glycidyl azide polyether of improved purity, said process comprising:
   a. forming a liquid reaction mixture consisting essentially of (i) polyethyleneoxide having a molecular weight between about 300 and 1000, (ii) sodium azide and (iii) polyepichlorohydrin having a molecular weight between about 500 and 10,000 wherein (i) and (iii) are miscible in each other at temperatures greater than about 80° C.;
   b. forming said glycidyl azide polyether in a reacted mixture by heating said reaction mixture at a temperature between about 80° and 120° C. for a time sufficient for displacement of the chloro groups of said polyepichlorohydrin with azido groups;
   c. removing said polyethyleneoxide from said reacted mixture by aqueous washings; and
   d. isolating said glycidyl azide polymer from the washed product of c.

2. The process in accordance with claim 1, wherein said reacted mixture is diluted with a water immescible liquid prior to said aqueous washings.

3. The process in accordance with claim 1 wherein said polyethyleneoxide has a molecular weight below about 1000.

4. The process in accordance with claim 2, wherein the weight ratio between (i) and (iii) is between about 10:1 and 0.5:1.

5. The process in accordance with claim 4, wherein the molar ratio between (ii) and (iii) is between about 1.05:1 and 1.5:1.

* * * * *

UNITED STATES PATENT AND TRADEMARK OFFICE
CERTIFICATE OF CORRECTION

PATENT NO. : 4,486,351
DATED : December 4, 1984
INVENTOR(S) : R. A. Earl  (Case 1)

It is certified that error appears in the above-identified patent and that said Letters Patent are hereby corrected as shown below:

Column 1, line 24;  "extact"  should read --exact-- .

Column 1, line 44;  "azid"  should read --azide-- .

Column 2, lines 35-39 of Formula III;

" " should read --

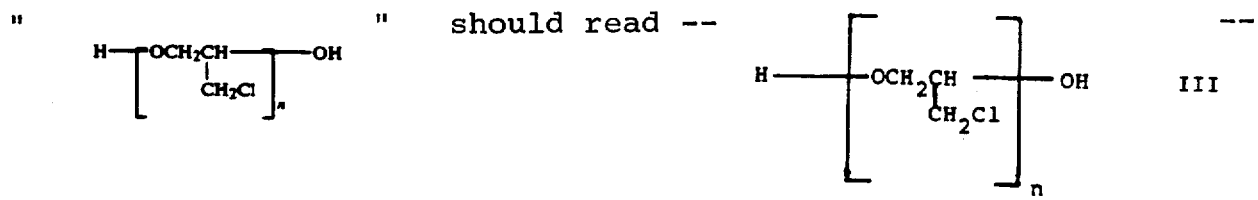

Column 3, lines 37-39; The following references have been omitted;

"(4) Used as received from Aldrich Chemical.
(5) Carried out using methods of W. R. Carpenter, Anal. Chem. 36, 2352 (1964).

Signed and Sealed this

Second Day of July 1985

[SEAL]

Attest:

DONALD J. QUIGG

Attesting Officer      Acting Commissioner of Patents and Trademarks